United States Patent
Smith

(10) Patent No.: US 9,161,932 B1
(45) Date of Patent: Oct. 20, 2015

(54) ANESTHETIC AND COOLING MIXTURE

(71) Applicant: Michael Smith, Columbus, GA (US)

(72) Inventor: Michael Smith, Columbus, GA (US)

(*) Notice: Subject to any disclaimer, the term of this patent is extended or adjusted under 35 U.S.C. 154(b) by 0 days.

(21) Appl. No.: 14/597,419

(22) Filed: Jan. 15, 2015

(51) Int. Cl.
*A61K 31/355* (2006.01)
*A61K 31/167* (2006.01)
*A61K 31/155* (2006.01)
*A61K 31/125* (2006.01)
*A61K 9/12* (2006.01)
*A61K 47/30* (2006.01)
*A61K 47/08* (2006.01)
*A61K 47/06* (2006.01)
*A61K 9/00* (2006.01)

(52) U.S. Cl.
CPC .............. *A61K 31/355* (2013.01); *A61K 9/0014* (2013.01); *A61K 9/124* (2013.01); *A61K 31/125* (2013.01); *A61K 31/155* (2013.01); *A61K 31/167* (2013.01); *A61K 47/06* (2013.01); *A61K 47/08* (2013.01); *A61K 47/30* (2013.01)

(58) Field of Classification Search
None
See application file for complete search history.

(56) References Cited

U.S. PATENT DOCUMENTS

| 4,938,960 | A | * | 7/1990 | Ismail | 424/745 |
| D364,339 | S | | 11/1995 | Shurtleff | |
| 8,187,574 | B2 | | 5/2012 | Mekata et al. | |
| 2005/0181036 | A1 | | 8/2005 | Aggarwai et al. | |
| 2010/0255130 | A1 | | 10/2010 | DeBaun et al. | |
| 2012/0128777 | A1 | | 5/2012 | Keck et al. | |
| 2013/0108557 | A1 | | 5/2013 | Abram et al. | |

FOREIGN PATENT DOCUMENTS

| EP | 0521455 | * | 1/1993 |
| EP | 0521455 A3 | | 1/1993 |

OTHER PUBLICATIONS

Pereira et al. "Polymeric films loaded with vitamin E and Aloe vera for topical application in the treatment of burn wounds," BioMed Research International, 2014, 9 pages.*

* cited by examiner

*Primary Examiner* — Alissa Prosser

(57) ABSTRACT

An anesthetic and cooling mixture is sprayed from an aerosol can and onto an injured area of a person. The mixture includes lidocaine, camphor, vitamin E, $H_2O$, polylactic acid and a propellant.

1 Claim, No Drawings

ANESTHETIC AND COOLING MIXTURE

BACKGROUND OF THE DISCLOSURE

1. Field of the Disclosure

The disclosure relates to skin cooling applications and more particularly pertains to a new skin cooling application for spraying on a person's skin where there person has sustained an injury to help cool the area and relieve pain.

2. Summary of the Disclosure

An embodiment of the disclosure meets the needs presented above by generally comprising a mixture which may be sprayed from an aerosol can. The mixture includes lidocaine, camphor, vitamin E, $H_2O$, polylactic acid and a propellant.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

DESCRIPTION OF THE PREFERRED EMBODIMENT

The principles and concepts of an embodiment of the disclosure will be described. The anesthetic and cooling mixture generally comprises a mixture of active ingredients including lidocaine, camphor and vitamin E. The vitamin E may include any number of vitamin E complexes including alpha-tocopherol and gamma-tocopherol, though any of the ten vitamin E forms may be utilized. $H_2O$ is added as solvent while polylactic acid may be added as a stabilizer. Further, one or more propellants may be used and my may include dimethyl ether and propane. Once the components stated above are formed into a mixture, the mixture is placed into a canister to allow the mixture to be released as an aerosolized topical treatment.

The mixture may vary but will typically include active ingredients having a weight ratio, with respect to each other, as the following:

- 1.0-3.0 parts lidocaine;
- 0.5-1.5 parts camphor;
- 0.5-1.5 parts vitamin E;
- 0.5-1.5 parts chlorhexidine gluconate.

The mixture may include by weight:
- 0.1-0.3 grams lidocaine;
- 0.05-0.15 grams camphor;
- 0.05-0.15 grams vitamin E;
- 0.5-1.5 grams chlorhexidine gluconate;
- 5.0-15.0 grams $H_2O$;
- 1.0-4.0 grams polylactic acid; and
- at least 25.0 grams of propellant.

The propellant may include between 25.0 and 100.00 parts by weight of dimethyl ether. Additionally, or alternatively, the propellant may include at least 15.0 parts by weight of propane.

The mixture defined above may include, more specifically by weight:
- 0.2 grams lidocaine;
- 0.1 grams camphor;
- 0.1 grams vitamin E;
- 0.1 grams chlorhexidine gluconate;
- 8.0 grams $H_2O$;
- 2.0 grams polylactic acid;
- 62.0 grams dimethyl ether; and
- 27.5 grams propane.

In use, the mixture is held within a canister, i.e. aerosol can, under pressure and may be sprayed therefrom onto a person's skin. Generally the mixture will be sprayed on areas where a person has muscle and joint pain, areas where surgery has been performed, sports injury areas and the like. The mixture will cool the area to reduce pain and to act generally as an anesthetic.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A topical anesthetic comprising:
    a mixture including:
    - 0.2 grams lidocaine;
    - 0.1 grams chlorhexidine gluconate;
    - 0.1 grams camphor;
    - 0.1 grams vitamin E;
    - 8.0 grams $H_2O$;
    - 2.0 grams polylactic acid;
    - 62.0 grams dimethyl ether; and
    - 27.5 grams propane.

* * * * *